United States Patent [19]

Mulqueen

[11] Patent Number: 5,314,661
[45] Date of Patent: May 24, 1994

[54] KIT OF TEST ELEMENTS AND LIQUID-BEARING CONTAINERS

[75] Inventor: Paul J. Mulqueen, Fairport, N.Y.

[73] Assignee: Eastman Kodak Company, Rochester, N.Y.

[21] Appl. No.: 990,164

[22] Filed: Dec. 14, 1992

[51] Int. Cl.$^5$ .................. G01N 1/28; B65D 83/10
[52] U.S. Cl. .......................... 422/57; 422/58; 422/61; 422/101; 221/220; 221/229
[58] Field of Search ............ 422/57, 61, 58, 101, 422/102; 221/220, 229–231; 206/222

[56] References Cited

U.S. PATENT DOCUMENTS

| Re. 30,595 | 4/1981 | Covington et al. | 422/63 |
| 3,276,156 | 10/1966 | Robinson | 206/456 |
| 4,152,390 | 5/1979 | Nosco et al. | 422/57 |
| 4,190,420 | 2/1980 | Covington et al. | 422/57 |
| 4,595,561 | 6/1986 | Thornton et al. | 422/58 |
| 4,981,805 | 1/1991 | Yazawa et al. | 436/169 |
| 4,994,238 | 2/1991 | Daffern et al. | 422/57 |

FOREIGN PATENT DOCUMENTS 191650  8/1986  European Pat. Off. ............ 422/57

Primary Examiner—James C. Housel
Assistant Examiner—Ramon Torres
Attorney, Agent, or Firm—Dana M. Schmidt

[57] ABSTRACT

A kit of slide-like articles that includes a stack of slide test elements and a separate stack of containers bearing a sealed liquid, the containers and test elements having substantially the same outside dimensions so that the containers are processable just like a slide test element. The seal of the container is penetratable by a pipette tip.

6 Claims, 1 Drawing Sheet

KIT OF TEST ELEMENTS AND LIQUID-BEARING CONTAINERS

FIELD OF THE INVENTION

This invention relates to a kit that supplies containers of liquid useful in a clinical analyzer that also uses slide test elements for assaying analytes, particularly containers bearing a diluent.

BACKGROUND OF THE INVENTION

It is known in clinical analyzers to use as the test vehicle, slide test elements bearing all the reagents in dried form as coatings in the test element, these elements being provided in a cartridge. See, for example, U.S. Pat. No. Re 30,595.

In a recently introduced analyzer available from Eastman Kodak Company under the trademark Ektachem 250, such test elements receive either a biological sample from a patient, or such a sample diluted with a diluent. The diluent can be used to predilute various body fluids (urine) for out of range samples, and to introduce additional reagents required. In that analyzer, dilution requires the use of special diluent-containing bottles and specialized mixing cups, both of which have to be handled at a separate station, with specialized equipment. Not only are such cups and bottles fairly large, compared to say, a test element, but also they can not be processed by the same automated handlers that move and process a test element.

Accordingly, prior to this invention, there has been a need for a simpler, smaller container to provide for dilution in an analyzer that uses slide test elements.

SUMMARY OF THE INVENTION

I have constructed a kit of slide-like articles that include containers that a) double both as the supplier of liquid for such dilution analyzers, and as the mixing vessel, and b) are capable of being handled exactly like a slide test element.

More specifically, there is provided a kit of slide-like articles for use in an analyzer, the kit comprising a stack of slide test elements, each element comprising dried layers at least one of which comprises one or more reagents necessary to produce a detectable change in the presence of an analyte, and a frame around the layers, and a stack of sealed slide-like containers bearing a liquid, the containers having substantially the same outside dimensions of width, length, and thickness as the slide test elements so that the containers are processable in an analyzer just like a slide test element.

Accordingly, it is an advantageous feature of the invention that a container of diluents is provided in small volumes that can be handled the same way a slide test element is handled.

It is a related advantageous feature of the invention that such a container can also function as a mixing vessel for mixing patient sample and diluent, thus eliminating the need for mixing cups separate from the original containers supplying the diluent.

Other advantageous features will become apparent upon reference the following Detailed Description, when read in light of the attached drawings.

DETAILED DESCRIPTION OF THE PREFERRED EMBODIMENTS

The description which follows is of slide-like articles of the preferred embodiments wherein the slide test elements are of a particular type, carried in cartridges of a particular construction, and wherein the liquid container contains a diluent. In addition, the kit invention is useful regardless of the type of slide test element used, regardless of the type of cartridge used or even the presence or absence of a cartridge, and regardless of the type of liquid in the container, be it diluent, reagent and otherwise.

The slide test elements are preferably any of those available under the trademark Ektachem from Eastman Kodak Company. Such elements bear all the needed reagents as dried coatings. They can be either colorimetric elements that produce a color for detection, or potentiometric elements that produce a differential voltage for detection.

Similarly, the cartridges preferably are those that come with such Ektachem slide test elements and which are shown in the aforesaid U.S. Pat. No. Re 30,595.

Figure 1:
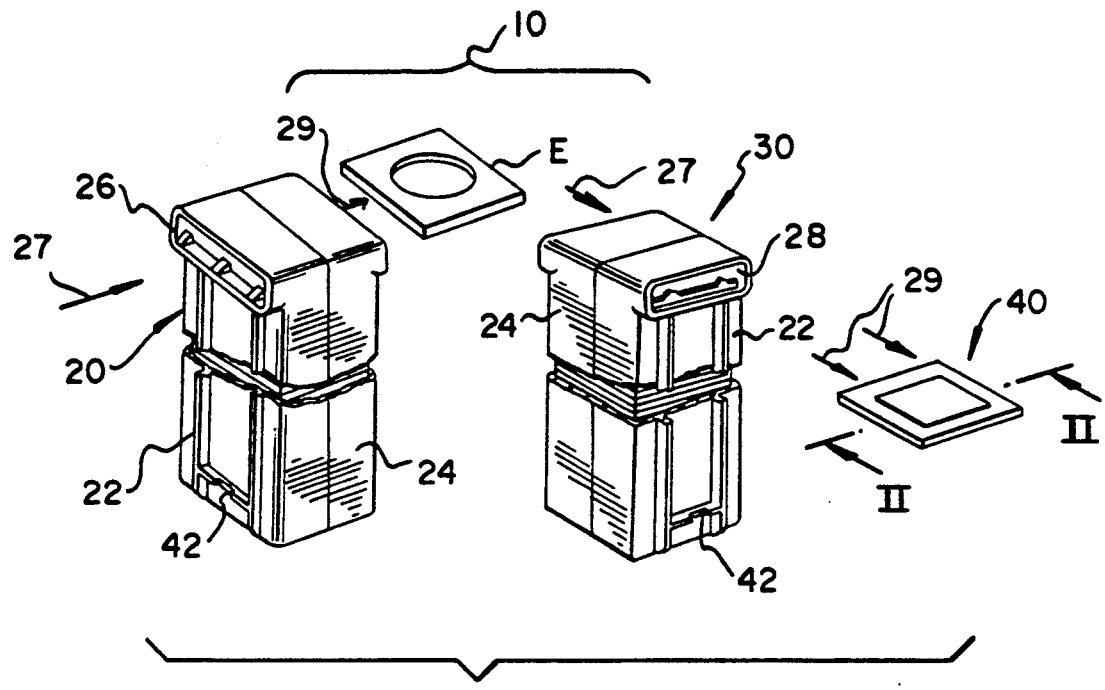
FIG. 1 is a fragmentary perspective view of the kit of the invention.

Referring now to FIG. 1, a kit 10 constructed in accordance with the invention comprises stacks of slide-like articles E and 40. Preferably it comprises at least a cartridge 20 of a stack of slide test elements E, which can be, e.g., for an immunoassay, and a cartridge 30 of a stack of diluent-bearing containers 40. Each of these cartridges 20 and 30 is substantially identical in configuration and size, for reasons explained hereinafter. As explained in Re. 30,595, they comprise side walls 22, end walls 24, an entrance aperture 26 for a pusher blade, arrow 27, an exit aperture 28 for either a test element E or container 40 to be ejected, arrows 29, and an anti-back-up platen (not shown) inside. Keying features, e.g., notches 42, can be used to ensure proper identification and/or orientation of cartridges 20 and 30.

Figure 2:
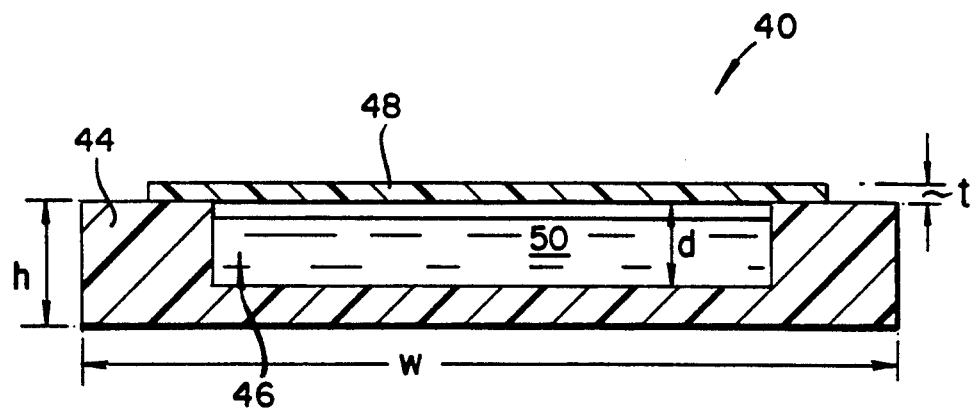
FIG. 2 is a section view taken generally along the plane II—II of FIG. 1.

The reason why the interior dimensions of cartridge 30 is preferably the same as for cartridge 20, is that the exterior dimensions of container 40, FIG. 2, namely "h", "w", and the length (not shown), are substantially identical for the counterpart dimensions of slide test element E. (The thickness "t" of cover 48, described hereinafter, is so negligible, e.g., about 0.08 mm, that it can be disregarded.)

Container 40 preferably comprises an impervious frame 44 recessed at 46 therewithin, a perforatable cover 48 completely sealing the recess 40 by, for example, adhesive pressure, ultrasonic bonding or by heat sealing, sealing also liquid 50 within the recess under cover 48. As noted, liquid 50 is preferably a diluent or additional reagent. Preferably, the volume of liquid 50 is less than the volume of recess 46 under cover 48, and most preferably at least 11 $\mu$L less. This amount of air gap (shown in FIG. 2) allows a liquid patient sample of 10 $\mu$L to be injected (described below) for mixing within container 40.

Representative interior dimensions of recess 46 effective to provide the above are a length of 14 mm, a width of 13 mm, and a depth "d", FIG. 2, of about 1.1 mm producing a total volume of 200 $\mu$L. The amount of diluent 50 preincorporated into recess 46 prior to sealing cover 48 would then be, e.g., about 189 $\mu$L. The addition of liquid sample of about 10 $\mu$L thus provides a dilution of about 19 to 1.

As used herein, the "perforatable" nature of cover 48 means that it is penetratable by a pipette tip exerting at least 57g (2 oz.) of force. Thin layers of aluminum foil with pressure sensitive adhesive are examples of materials that are perforatable. As such, cover 48 readily seals in liquid 50 until such time as an aspirating tip punctures it, and dispenses an aliquot (e.g., 10 μL) of sample into recess 46 and liquid 50. Another tip then repeatedly aspirates out and redispenses the mixture into container 40 to effect mixing. Following mixing, most of the diluted liquid in container 40 is aspirated out for dispensing onto a slide test element E.

As used in the analyzer, cartridge 30 would be placed at a slide supply station along with cartridges 20, and containers 40 ejected using preferably the same pusher blade (not shown) as is used on cartridges 20. Container 40 would then be transported by the same mechanisms used to transport slide test elements E, to the metering station where a pipette tip already has in it a patient sample. That tip would puncture cover 48 and dispense an aliquot, e.g., 10 μL, and then be withdrawn and discarded or used with another, fresh container 40 or slide test element E. A new tip is then picked up, and this tip is used to aspirate and redispense out of and into container 40, the mixture of liquids, and finally to reaspirate the now mixed liquids for dispensing onto a slide test element E.

As an alternative, liquid 50 of container 40 can be used for pretreating a slide test element, or for introduction of a reagent such as an antibody or competitive ligand which is not already pre-incorporated into slide test element E. In such cases, the mixing step and function of container 40 is eliminated.

For convenience, cartridges 20 and 30 can be boxed together, or separately.

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. A kit of slide articles for use in an analyzer, said kit comprising:
   a stack of slide test elements, each element comprising dried layers at least one of which comprises at least one reagent necessary to produce a detectable change in the presence of an analyte, and a frame around said layers; and
   a stack of sealed slide containers bearing a predetermined reagent liquid, said containers having substantially the same outside dimensions of width, length and thickness as said slide test elements so that said containers are processable in an analyzer just like a slide test element.

2. A kit as defined in claim 1, wherein each of said containers comprises:
   an impervious frame having a liquid-confining recess within the frame, and
   a perforatable cover completely sealing over said recess, said liquid being sealed with said recess and said frame, under said cover.

3. A kit as defined in claim 2, wherein said liquid is present in an amount less than the total void volume between said cover and said frame, so that said container also functions as a mixing vessel with room to receive a patient sample.

4. A kit as defined in claim 3, wherein said liquid is a diluent.

5. A kit as defined in claim 1, wherein said liquid is a diluent.

6. A kit as defined in claim 1, wherein said stack of said slide test elements and said stack of slide containers are each contained in a cartridge, said cartridge of said slide containers being substantially identical in size and structure as said cartridge of said slide test elements.

* * * * *